United States Patent [19]

Kawasaki et al.

[11] Patent Number: 5,052,926

[45] Date of Patent: Oct. 1, 1991

[54] PALLET FOR HANDLING DENTAL PORCELAIN MATERIALS

[75] Inventors: Tsugumichi Kawasaki, Nagoya; Hiroyuki Hino, Ichinomiya, both of Japan

[73] Assignee: G-C Toshi Kogyo Corporation, Kasugai, Japan

[21] Appl. No.: 500,992

[22] Filed: Mar. 29, 1990

[30] Foreign Application Priority Data

Apr. 5, 1989 [JP] Japan ................................. 1-84643
Dec. 27, 1989 [JP] Japan ................................. 1-33636

[51] Int. Cl.$^5$ ........................... A61C 1/14; A61C 3/04
[52] U.S. Cl. ......................................... 433/49
[58] Field of Search ................ 433/25, 49, 163; 206/368, 63.5; 269/302.1

[56] References Cited

U.S. PATENT DOCUMENTS

| | | | |
|---|---|---|---|
| 1,278,153 | 9/1918 | Jefferies | 433/49 |
| 1,539,428 | 5/1924 | Romaine | 433/49 |
| 1,980,533 | 7/1932 | Kile | 433/49 |
| 1,982,155 | 4/1933 | Earman | 433/49 |
| 1,993,450 | 3/1935 | Lowry | 269/302.1 |
| 4,812,119 | 3/1989 | Hewitt | 433/49 |

FOREIGN PATENT DOCUMENTS 0005002 10/1979 European Pat. Off. .............. 433/49

*Primary Examiner*—John J. Wilson
*Assistant Examiner*—Cinoy A. Cherichetti
*Attorney, Agent, or Firm*—Oblon, Spivak, McClelland, Maier & Neustadt

[57] ABSTRACT

A pallet for handling water-permeable dental porcelain materials comprises a porous ceramic material formed of one or two or more selected from the group consisting of materials based on alumina, aluminium silicate, mullite, cordierite, zirconia and vitreous china and having a grain size of 1.0 to 30.0 μm and a mean grain size of 1.5 to 25.0 μm. The porous ceramic material having fine and even pores uniformly dispersed therethrough, as expressed in terms of a porosity of 15 to 65% and a mean pore size of 0.5 to 10 μm.

7 Claims, No Drawings

PALLET FOR HANDLING DENTAL PORCELAIN MATERIALS

BACKGROUND OF THE INVENTION

1. Field of the Invention

The present invention relates to a pallet for handling dental porcelain materials, which is used to prepare procelain crowns such as porcelain crowns with metals baked to them and porcelain jacket crowns, and always keeps the consistency of a dental porcelain slurry constant for successful porcelain handling.

2. Prior Art

Heretofore, porcelain crowns such as porcelain crowns with metals baked thereon and porcelain jacket crowns have been prepared by placing a suitable amount of the dental porcelain powders used upon a porcelain kneading pallet (hereinafter called simply the pallet), adding thereto a suitable amount of distilled water or a kneading liquid exclusive to porcelain materials (hereinafter referred simply to the kneading liquid), kneading them with a metallic spatula or the like into a slurry having a certain consistency, and placing a suitable amount of the dental porcelain slurry on a metal frame or model with the use of a brush, a metallic spatula or the like for firing or calcination.

Hitherto, glass plate, Teflon plate or vitreous china plate with glaze put on their surfaces have been used as the kneading pallets for mixing the dental porcelain powders with distilled water or the kneading liquid into a dental porcelain material slurry and preserving it until it is used for dental handling.

When porcelain crowns such as porcelain crowns with metals baked thereon and porcelain jacket crowns are to be prepared, however, the distilled water or kneading liquid, contained in the dental porcelain material slurry preserved on the pallet, diffuses slowly in the air, so that the slurry can be dried or solidfied within a few minutes to about 10 minutes to such an extent that it cannot be handled, thus making it impossible to place it on the metal frame, etc. with a brush or metallic spatula. Consequently, the dental porcelain slurry should again be kneaded with a suitable amount of distilled water or the kneading liquid. This was troublesome and inconvenient because dental handling could not stably be carried out at a certain consistency.

There have been some dental porcelain material kneading pallets designed to supply distilled water or the kneading liquid to a dental porcelain material on a dental porcelain material kneading plane by some means. As one of such pallets, there has been proposed a dental porcelain material kneading pallet (Japanese Patent Application No. 42588/1979, entitled "MIXING TRAY ASSEMBLY") which comprises a vitreous china plate with glassy glaze put on its surface and an opening formed in its dental porcelain material kneading material plane and a cotton core passed through said opening, as is the case with an alcohol lamp's wick, thereby sucking up distilled water or a kneading liquid exclusive to dental porcelain materials from the bottom of the pallet. A grave problem with this assembly has been that the distilled water or kneading liquid penetrates only through the core's periphery of the kneading plane, thus failing to make the whole dental porcelain slurry have a certain consistency.

Other dental porcelain material kneading pallets have been available, in which no glassy glaze is put on a part of a dental porcelain material kneading plane of a vitreous china plate located on the upper face of a closed case, or pores of about 1 mm in diameter are provided in the kneading plane, thereby sucking up distilled water or a kneading liquid exclusive to porcelain materials due to a water pressure difference owing to a difference in height between the liquid level in an inlet hole and the kneading plane. A grave problem with these has been that because the distilled water or kneading liquid is caused to ooze out on the kneading plate due to a difference in height between the liquid level in the inlet hole and the kneading plane, the liquid level in the case is so likely to change that there can be a drop of the liquid pressure, which in turn makes the oozing of the distilled water or kneading liquid onto the kneading plane unstable and so makes it impossible to impart a certain consistency to the dental porcelain material slurry.

More recently, a dental porcelain material kneading pallet having only a portion of its upper face, on which a dental porcelain material is to be kneaded, left intact with no glaze put thereon, i.e., unglazed has been proposed for a conventional dental porcelain material kneading pallet formed of porcelain and having its overall surface made smooth by putting glassy glaze thereon. This pallet formed of porcelain is placed on a tray through sponge. Then, distilled water or the kneading liquid is charged in the tray to a height of about 5 mm from the tray's face, whereby it is sucked from the bottom of the pallet into the body of the pallet through the sponge and then reaches the dental porcelain material kneading portion defined by the upper face of the pallet. Thus, the distilled water or kneading liquid is supplied to the kneaded dental porcelain slurry, thereby assuring that its consistency is always kept constant.

However, such a dental porcelain pallet has posed various difficult-to-solve problems, as mentioned below.

(1) For the very reason that it is formed of vitreous china and partly left intact or unglazed, its surface is so rough, as expressed in terms of a centerline surface roughness of 15 $\mu$m, that the dental porcelain slurry can be brushed out with difficulty and that the brush is prematurely worn down.

(2) For the same reason that its surface is very rough, a metallic spatula used for mixing the dental porcelain powders with distilled water or the kneading liquid is so likely to be worn down by contact with the porcelain's surface. Powders resulting from the abrasion of the metallic spatula or the pallet may contaminate the dental porcelain slurry to make the prepared porcelain crown cloudy.

(3) The pallet is formed of a conventional vitreous china material with no modification made to it, so that it differs largely in particle size, i.e., has a very wide particle size distribution. In consequence, the porcelain pallet varies so largely in pore diameter that the penetration of distilled water or the kneading liquid from the bottom of the pallet to the porcelain material kneading plane becomes unstable, thus making it difficult to keep the consistency of the dental porcelain slurry constant and hence dental handling is made difficult.

(4) As stated in (3), the dental porcelain pallet varies so largely in pore diameter that it varies in porosity from place to place or, to put it another way, pores are not uniformly dispersed throughout the pallet. For that reason, insufficient penetration of distilled water or the kneading liquid is more likely to occur on the pallet's ends than the pallet's central region. This results in the consistency of the dental porcelain slurry becoming uncertain and so often needs repeated kneading, which makes its dental handling difficult.

(5) When the porcelain pallet is immersed in distilled water, etc. over an extended period of time, it becomes unhygienic since its kneading plane is covered with mold due to its large pore diameter.

(6) In use, sponge is placed as a cushion between the porcelain pallet and the case so as to suck up moisture through the pallet in a stable manner. Since the pallet is overlaid on the sponge so that it is spaced away from the case, however, it tends to be so unstable when the dental porcelain slurry is kneaded or brushed out that its dental handling becomes difficult.

A primary object of the present invention is to provide a solution to the above problems which make it impossible to carry out dental handling and to prepare porcelain crowns in a rapid and effective manner, whereby the problems of the conventional water-permeable dental porcelain material-handling pallets that they have uneven pore sizes, not uniform pore size distribution and large surface areas can be eliminated successfully. In consequence, it is unlikely that metallic spatulas or pallets may be worn down at the time of kneading dental porcelain slurries and it is assured that the dental porcelain slurries are well brushed out with no abrasion of the brushes, thus making it possible to carrying out dental handling in speedy manners.

SUMMARY OF THE INVENTION

In order to achieve this object, the present invention makes use of porous ceramics based on alumina, aluminium silicate, mullite, cordierite, zirconia and vitreous china in which aggregate grains are elaborately regulated to a grain size of 1.0 to 30.0 μm and a mean grain size of 1.5 to 25.0 μm, said porous ceramics having its mean pore size derived from inter-aggregate gaps and its pore size determined by carrying out calcination in such a way that no growth of the aggregate grain takes place at the time of calcination.

The thus obtained porous ceramic pallet for handling dental porcelain materials has its mean pore size ranging from 0.5 to 10.0 μm and its pores distributed uniformly throughout it, as expressed in terms of a porosity ranging from 15% to 65%, and is characterized in that its kneading plane has a centerline surface roughness as fine as 2.0 μm or below. Distilled water or the kneading liquid is thus sucked up through the porous ceramics from its bottom due to capillary action to make the consistency of a dental porcelain slurry constant.

Porous ceramics based on alumina, aluminium silicate, mullite, cordierite, zirconia and vitreous china, in which aggregate grains are regulated to a mean grain size less than 1.5 μm, come to have a mean pore size less than 0.5 μm. This is too small to take up distilled water, thus causing the take-up rate of water to be delayed. When distilled water is used, the ceramic pallet should preferably have a mean pore size ranging from 0.5 μm to 10 μm. When the kneading liquid is used, on the other hand, the ceramic pallet should preferably have a mean pore size ranging from 1.0 μm to 10 μm, since water-soluble high molecules in the kneading liquid are entrapped in the porous ceramics at too small pore sizes, so that the effect of the kneading liquid becomes limited.

When the aggregate grains are regulated to a mean grain size larger than 25.0 μm, the porous ceramics come to have a mean pore size exceeding 10 μm. In this case, the pores' sizes are so increased that the taking-up of water becomes not uniform, thus making it difficult to keep the consistency of a dental porcelain material slurry constant. In addition, the pallet comes to have a more increased surface roughness, so that the brush becomes unwieldy when dishing out a dental porcelain slurry.

Hence, limited to the range of 0.5 μm to 10 μm is the mean pore size of the porous ceramics based on alumina, aluminium silicate, mullite, cordierite, zirconia and vitreous china in which aggregate grains are carefully regulated to the desired grain size distribution, i.e., a grain size of 1.0 to 30.0 μm and a mean grain size of 1.5 to 25.0 μm.

When porous ceramics usable as the materials of pallets for handling dental porcelain materials are less than 15% in porosity, they are unpractical because the take-up rate of distilled water or the kneading liquid is slow. At a porosity higher than 65%, on the other hand, the pores account for a larger volume of the porous ceramics, so that they become fragile and thus unpractical.

Hence, limited to the range of 15% to 65% is the porosity of porours ceramics prepared with grains based on alumina, aluminium silicate, mullite, cordierite, zirconia and vitreous china.

In order to prevent the porous ceramics from getting moldy, it is desired to add antibacterial zeolites thereto. Preferably, the antibacterial zeolites should be of a structure in which the ion-exchangeable ions are partly or wholly substituted by ammonium ions and antibacterial metal ions. In the present invention, use may be made of suitable zeolites, whether natural or synthetic, which are generally of a three-dimensional skeleton structure, as expressed by the following general formula:

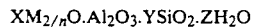

$XM_{2/n}O.Al_2O_3.YSiO_2.ZH_2O$ wherein:
M is the ion-exchangeable ion, usually a monovalent or divalnet metal ion,
n is the valence of a (metal) ion,
X and Y each are the index of a metal oxide and silica, and
Z is the number of water of crystallization.

Illustratively but not exclusively, use may be made of A type zeolite, X type zeolite, Y tye zeolite, T type zeolite, high-silica zeolite, sordalite, mordenite, analcime, cryptolite, chabasite and erionite. These zeolites have a sufficient volume to be exchangeable with antibacterial metal ions, say, 7 meq/g for A type zeolite, 6.4 meq/g for X type zeolite, 5 meq/g for Y type zeolite, 3.4 meq/g for T type zeolite, 11.5 meq/g for sordalite, 2.6 meq/g for mordenite, 5 meq/g for analcime, 2.6 meq/g for cryptolite, 5 meq/g for chabasite and 3.8 meq/g for erionite. Usable in the present invention are the above zeolites in which the ion-exchangeable ions, e.g., sodium, calcium, potassium, magnesium and iron ions, are partly or wholly substituted by antibacterial metal ions, preferably ammonium ions. Illustrative examples of the antibacterial metal ions are ions of silver, copper, zinc, bismuth and thallium, preferably those of silver, copper and zinc. Suitably, the above antibacterial metal ions should be contained in the zeolite in an amount of 0.1 to 15%, since they also show an antimicrobial action. More preferably, the antibacterial zeolite should contain 0.1 to 15% of silver ions and 0.1 to 8% of copper ions. While ammonium ions may be contained in the zeolite in an amount up to 20%, on the other hand, it is preferred that they be contained in the zeolite in an amount of 0.5 to 5%, particularly 0.5 to 2%, since they can effectively prevent the discoloration of that zeolite. In the present disclosure, the unit "%" refers to weight % on 110° C.-dry basis.

In what follows, how to prepare the antibacterial zeolites used in the present invention will be explained. For instance, they may be prepared by bringing a zeolite into contact with a mixed aqueous solution containing pre-regulated antibacterial metal ions such as those of silver, copper and zinc and, more preferably, including ammonium ions, thereby substituting the ion-exchangeable ions in the zeolite by the above ions. The contact may be carried out at 10° to 70° C., preferably 40° to 60° C. for 3 to 24 hours, preferably 10 to 24 hours in a batchwise or continuous (e.g., columnar) manner. Suitably, the mixed aqueous solution is regulated to pH 3 to 10, preferably 5 to 7. Said regulation makes it possible to prevent the oxide of silver, etc. from being deposited on the surface of zeolite or in the pores of zeolite. The respective ions in the mixed aqueous solution may all be supplied in the form of salts. For instance, ammonium ions may be supplied in the form of ammonium nitrate, sulfate, acetate, perchlorate, thiosulfate or phosphate; silver ions in the form of silver nitrate, sulfate, perchlorate or acetate or diammime silver nitrate or sulfate; copper ions in the form of copper nitrate (II), copper perchlorate, copper acetate, potassium tetracyanocuprate or copper sulfate; zinc ions in the form of zinc sulfate (II), sulfate, perchlorate, thiocyanate or acetate; bismuth ions in the form of bismuth chloride or iodide; and thallium ions in the form of thallium perchlorate, sulfate, nitrate or acetate.

Optionally, the contents of ammonium ions, etc. in the zeolite may be controlled by regulating the concentrations of the respective ions (salts) in the above mixed aqueous solution. For instance, when the antibacterial zeolite contains ammonium and silver ions, it is possible to obtain an antibacterial zeolite containing 0.5 to 5% of ammonium ions and 0.1 to 5% of silver ions by regulating the concentrations of ammonium and silver ions in the mixed aqueous solution to 0.2 M/l to 2.5 M/l and 0.002 M/l to 0.15 M/l, respectively. When the antibacterial zeolite further contains copper and zinc ions, it is possible to obtain an antibacterial zeolite containing 0.1 to 8% of copper ions and 0.1 to 8% of zinc ions by regulating the concentrations of copper and zinc ions in the mixed aqueous solution to 0.1 M/l to 0.85 M/l and 0.15 M/l to 1.2 M/l, respectively.

Alternatively, the ion exchange may be carried out by bringing aqueous solutions each containing single ions, rather than such a mixed aqueous solution as mentioned above, into successive contact with the zeolite. The concentrations of the respective ions in the respective aqueous solutions may be determined, as is the case with the concentrations of the respective ions in the mixed aqueous solution.

After the completion of the ion exchange, the zeolite is fully washed with water and, then, dried preferably at 105° to 115° C. at normal pressure or at 70° to 90° C. under reduced pressure (1 to 30 torr). It is noted that for the ion exchange of ions for which no suitable water-soluble salts are found such as, for instance, lead or bismuth or organic ions, the reaction may be carried out with an organic solvent solution such as alcohol or acetone, while avoiding any precipitation of slightly soluble basic salts.

Suitably, these antibacterial zeolites may be added to 100 parts by weight of the porous ceramics in an amount of preferably 0.005 to 15 parts by weight, more preferably 0.01 to 5 parts by weight. At less than 0.005 parts by weight, they are so less effective for mold that when the pallet is left wet over an extended period of time, it gets moldy and so becomes unhygienic. At higher than 15 parts by weight, on the other hand, they are effective for mold, but render it difficult to mold pallets. Even though pallets can be formed, they are useless since they decrease in strength and turn reddish brown.

Next, how to prepare the pallets according to the present invention will be explained.

The raw materials used are alumina systems in which alumina powders ($Al_2O_3$) are used as aggregate grains with a binder of alumina glass; aluminium silicate systems in which vitreous china chamotte is used as aggregate grains with a binder of glassy flux; mullite systems in which mullite ($3Al_2O_3.2SiO_2$) and quartz ($SiO_2$) are used as aggregate grains with a binder of anorthite; cordierite systems in which cordierite powders ($2MgO.2Al_2O_3.5SiO_2$) are used as aggregate grains with a binder of K feldspar and alumina glass; zirconia systems in which electrically molten, crude zirconia powders ($ZrO_2$) are used as aggregate grains with a binder of finely divided zirconia powders; and vitreous china systems in which vitreous china chamotte is used as aggregate grains with a binder of glassy flux.

The aggregate grains of each ceramic are then carefully regulated to the desired grain size, i.e., the grain size ranging from 1.0 to 30.0 $\mu$m and the mean grain size ranging from 1.5 to 25.0 $\mu$m by suitable means such as vibratory screening, pneumatic classification and levigation. Subsequently, they are mixed with the binder of each ceramic having its grain size regulated in a similar manner together with 5 to 30 parts of a binder aid such as water glass, dextrin or polyvinyl alcohol to make a green body, which is then moled or otherwise formed to obtain a green mold. In the case of wet molding, water is further added to a similar mixture to form a slurry, which is then cast in a gypsum mold, dried and released from the mold, thereby preparing a green mold.

When the antibacterial zeolite is added, its predetermined amount may be added in a well-dispersed state at the time of mixing each ceramic and the binder together with the binder aid.

The thus molded green mold is well-burned to remove the organic components such as the binder aid, and is then calcined at a temperature ranging from 1000° C. to 1400° C. into a porous ceramic product in which fine and even pores having a mean pore size of 0.5 to 10 $\mu$m are uniformly dispersed at a porosity of 15 to 65%.

A calcination temperature exceeding 1400° C. is unpreferred, since the aggregate grains grow to so large a size at the time of calcination that the inter-grain gaps decrease and that the mean pore size of the ceramic is too decreased to take up distilled water or the kneading liquid. At a calcination temperature lower than 1000° C. on the contrary, no sufficient fusion of the aggregate grains takes place, so that the calcined porous ceramic becomes fragile and so unpractical.

Hence, limited to 1000° C. to 1400° C. inclusive is the temperature at which the particles based on alumina, aluminium silicate, mullite, cordierite, zirconia and vitreous china are calcined into porous ceramics for the pallets for handling dental porcelain materials.

The dental pallet formed of the porous ceramic body prepared under the above conditions is placed in a plastic tray, in which distilled water or the kneading liquid is then filled to a height of 2 mm from the tray's plane. Tens of seconds later, distilled water or the kneading liquid is uniformly picked up on the kneading plane through capillary actions, thereby keeping the consistency of a dental porcelain material slurry constant. The pallet is also stable due to no need of interposing sponge between it and the tray.

The conventional systems for supplying distilled water or the kneading liquid onto the kneading plane within the closed case by locating the liquid inlet at a position above the kneading plane has posed a grave problem, because it is designed to supply distilled water or the kneading liquid onto the kneading plane due to a difference in height. This results in a drop of water pressure, which in turn causes an unstable supply of distilled water or the kneading liquid, thus failing to keep the consistency of a dental porcelain material slurry constant.

EXAMPLES

The present invention will now be explained specifically but not exclusively with reference to the following examples.

The raw materials used in the examples are alumina systems in which alumina powders are used as aggregate grains with a binder of alumina glass; aluminium silicate systems in which vitreous china chamotte is used as aggaregate grains with a binder of glassy flux; mullite systems in which mullite and quartz are used as aggregate grains with a binder of anorthite; cordierite systems in which cordierite powders are used as aggregate grains with a binder of K feldspar and alumina glass; zirconia systems in which electrically molten, crude zirconia powders are used as aggregate grains with a binder of finely divided zirconia powders; and vitreous china systems in which vitreous china chamotte is used as aggregate grains with a binder of glassy flux. The aggregate grains are then carefully regulated to the desired grain size distribution, i.e., the grain size ranging from 1.0 to 30.0 μm and the mean grain size ranging from 1.5 to 25.0 μm. Subsequently, they are mixed with a binder aid such as water glass, dextrin or polyvinyl alcohol to make a green body, which is then placed in a mold for molding. The thus molded green mold is well-burned to remove the organic binder, etc. used for molding, and is then calcined.

Reference will now be made to the properties estimated and the procedures applied for estimation.

WATER PERMEABILITY

A test piece (100×100×10 mm) formed of each ceramic material was placed in a plastic tray, in which distilled water or the kneading liquid was then filled to a height of about 2 mm to immerse the test piece therein. After the test piece was allowed to stand for one minute, whether distilled water or the kneading liquid was picked up on the upper plane of the test piece was relatively estimated with respect to the reference target.

SURFACE ROUGHNESS

The mean centerline surface roughness of a test piece was measured with a contact type of surface roughness meter.

MEAN PORE SIZE AND POROSITY

The mean pore size and porosity of a test piece were measured with a mercury-filled type of porosimeter. Assuming that the pores were in cylindrical forms, the mean pore size was found by dividing the entire pore volume by the pores' specific surface areas. The porosity was found by dividing the volume of the pores in which mercury was filled by the volume of the test piece.

OCCURRENCE OF MOLD

The test piece used for the estimation of water permeability was held as such in a desiccator maintained at 37° C. and a humidity of 100% for one week to visually observe whether or not the upper plane of the test piece got moldy.

CONTAMINATION OF DENTAL PORCELAIN MATERIAL WITH POWDERS RESULTING FROM ABRASION

Suitable amounts of transparent dental porcelain powders for metal-baking and distilled water or the kneading liquid were dished out on the kneading plane of a test piece, and were then well-kneaded together for one minute by means of a metallic spatula into a dental porcelain slurry. The slurry was placed on a palladium foil for the fused of dental porcelain materials and fully rid of moisture. Then, it was calcined in a dental electric furnace according to conventional procedures to visually observe how much the fused dental porcelain material became cloudy.

UNIFORMITY OF PORE DISTRIBUTION

Ink was dropped on a dry test piece from a dropper for the relative estimation of the diameters of the ink spot at its central region and both end regions.

The alumina base porous ceramics prepared using alumina powders as aggregate grains and alumina glass as a binder (Examples 1-1, 1-2, 1-3, 1-4 and 1-5), the aluminium silicate base porous ceramics prepared using vitreous china chamotte as aggregate grains and glassy flux as a binder (Examples 2-1 and 2-2), the mullite base porous ceramics prepared using mullite and quartz as aggregate powders and anorthite as a binder (Examples 3-1, 3-2 and 3-3), the cordierite base porous ceramics prepared using cordierite powders as aggregate powders and alkali feldspar and alumina glass as a binder (Examples 4-1, 4-2 and 4-3) and the zirconia base porous ceramics prepared using electrically molten crude zirconia powders as aggregate powders and finely divided zirconia powders (Examples 5-1 and 5-2) were all water-permeable, had a mean pore size as small as 0.5 to 10 μm and a porosity of 15 to 65% and allowed distilled water or the kneading liquid to permeate constantly therethrough. Their centerline surface roughness was as fine as 0.9 to 2.5 μm, so that the brush could successfully be handled at the time of handling dental porcelain materials with no substantial abrasion.

In Examples 6 to 10, dental pallets were prepared with porous ceramics to which antibacterial zeolites were added. The porous ceramics obtained in Examples 6-10 were based on alumina, aluminium silicate, mullite, cordierite and zirconia. In Examples 6 and 7, the antibacterial zeolite used was A type zeolite and in Examples 8 and 9, the antibacterial zeolite used was X type zeolite. In Example 10, two antibacterial zeolites, i.e., A type zeolite and X type zeolite were used. These porous ceramics all posed no problem in connection with the properties estimated, since the amount of the antibacterial zeolites added came within the range as recited in the appended claims. In addition, these pallets were much more improved in the antimycotic effect than the dental pallets of Examples 1-5 in which no antibacterial zeolite was added.

As will be clearly understood from tables to be given later, conventional dental pallets (Comparative Examples 1-3) formed of glass, Teflon and porcelain with glassy glaze put on its entire surface showed no sign of getting moldy and contaminating dental porcelain materials with powders resulting from abrasion, but were so totally free from water permeability that it was impossible to constantly maintain the consistency of a dental porcelain slurry constant, thus making dental handling difficult.

A dental pallet (Comparative Example 4), only the kneading plane of which was partly glazed with glass, was water permeable, but had a mean pore size as large as 20 μm, so that difficulty was encountered in keeping the taking-up of distilled water or the kneading liquid constant. Its surface roughness was as coarse as 1.5 μm, thus making the brush unwieldy at the time of dental handling with its increased abrasion and with the contamination of a dental porcelain material with powders resulting from abrasion. The pallets also got moldy.

A dental pallet (Comparative Example 5) formed of porous ceramics having a mean grain size of 0.8 μm and a grain size distribution of 0.6 to 0.9 μm had a surface roughness as fine as 0.5 μm. It was water-permeable, but was unpractical since its mean pore size was as small as 0.3 μm, thus causing delayed water permeation. However, the pallet did neither get moldy nor contaminate a dental porcelain material with powders resulting from abrasion.

When the kneading plane designed to supply distilled water or the kneading liquid due to a difference in water pressure was made porous (Comparative Example 6), the pallet was water-permeable, but made water penetration uncertain because of a difference in hydrostatic pressure. The pallet was also as coarse as 15 μm in its surface roughness, thus making the brush unwieldy at the time of dental handling with its increased abrasion. Further, the pallet got moldy with the contamination of a dental porcelain material with powders resulting from abrasion.

When a hole of 1 mm was formed in the kneading plane in the same system, distilled water or the kneading liquid oozed out due to a difference in hydrostatic pressure. However, the oozing of distilled water or the kneading liquid became uncertain due to that difference in hydrostatic pressure and was excessively deposited around the hole, thus making it difficult to keep the consistency of a dental porcelain slurry constant. Dental porcelain powders were also caught in the hole, thus making it difficult to clean the pallet (Comparative Example 7).

A system in which a cotton core like an alcohol lamp's wick was inserted through a hole formed in a kneading plane of a dental porcelain pallet sheet with glassy glaze put on its surface to pick up distilled water or the kneading liquid from the bottom of the pallet is unpreferred, since distilled water or the kneading liquid is picked up only around the core on the kneading plane, thus failing to obtain a dental porcelain slurry has a certain consistency as a whole. Dental porcelain powders are also caught in the core portion, thus making it difficult to clean the pallet (Comparative Example 8).

A pallet (Comparative Example 9) formed of porous ceramics having a porosity of 70% is unpreferable, since the ceramics is fragile and contaminates a dental porcelain material.

Although a pallet (Comparative Example 10) formed of porous ceramics having a porosity of 15% is water-permeable, it is unpractical because the rate of permeation of ditilled water or the kneading liquid through it is slow.

Comparative Examples 11 to 15 were carried out to determine the amount of antibacterial zeolites added to porous ceramics. In Comparative Examples 11 and 13, the amount of the antibacterial zeolites, i.e., A type zeolite and X type zeolite added to the porous ceramics are below the lower limit as recited in the appended claims. In a smaller amount, the antibacterial zeolites are less effective for mold. In Comparative Examples 12 and 14, the amount of the antibacterial zeolites are higher than the upper limit as recited in the appended claims. The antibacterial zeolites are even more effective for mold in a larger amount. However, since they take no part in sintering, the dental pallet comes to have a centerline surface roughness so increased that its surface becomes rough, thus making it difficult to use the pallet. Molten matters of the zeolites serve to lower the water permeability of the dental pallet, and the reddish brown of the metal ions contained in the antibacterial zeolites are transferred to the dental pallet. In Comparative Example 15, two antibacterial zeolites, i.e., A type zeolite and X type zeolite, are used in the respective amounts coming within the range as recited in the appended claims. Although the dental pallet is much more effective for mold because the combined amount of the two zeolites exceeds the upper limit as recited in the appended claims, it can only be used with difficulty, since its surface becomes rough. Its water permeability is reduced. In addition, the color of the metal ions contained in the antibacterial zeolites is transferred to the dental pallet.

The above examples are all based on alumina, aluminium silicate, mullite, cordierite and zirconia. It is noted, however, that there is no difference in performance between the compositions of ceramic materials. Other ceramic materials shows similar performance, if they provide porous ceramics having a mean pore size of 0.5 to 10 μm and having fine and uniform pores dispersed throughout it, as expressed in terms of a porosity of 15 to 65%.

The results are tabulated in Tables 1 to 4, wherein:
in connection with water permeability,
x indicates that the test piece has no water permeability;
  indicates that the test piece is water-permeable but unstable;
indicates that the test piece is water-permeable but the rate of permeation of water through it is slow; and
○ indicates that the test piece has improved water permeability;
in connection with the occurrence of mold,
x indicates that the test piece gets moldy;

○ indicates that the test piece does not get moldy; and

⊙ indicates that the test piece does not get moldy over extended periods of time;

in connection with how much the test piece becomes cloudy, x indicates that the test piece becomes cloudy; and ○ indicates that the test piece does not become cloudy; and in connection with the uniformity of pore distribution, x indicates that there is a difference between the central region and both end regions of the test piece;

○ indicates that there is no difference between the central region and both end regions of the test piece; and "no pore" indicates that the test piece contains no pore.

TABLE 1

| Example | Composition | | | | | | Mean grain size (μm) | Grain size distribution (μm) | Mean pore size (μm) |
|---|---|---|---|---|---|---|---|---|---|
| | | $Al_2O_3$ | $SiO_2$ | | | | | | |
| 1-1 | Alumina | 97.0 | 3.0 | | | | 2.0 | 1.1~2.8 | 0.6 |
| 1-2 | | 95.0 | 5.0 | | | | 2.5 | 1.5~3.5 | 0.9 |
| 1-3 | | 90.0 | 10.0 | | | | 6.0 | 2.0~10.0 | 2.0 |
| 1-4 | | 85.0 | 15.0 | | | | 15.0 | 10.0~20.0 | 5.0 |
| 1-5 | | 80.0 | 20.0 | | | | 25.0 | 23.0~28.0 | 8.0 |
| | | $Al_2O_3$ | $SiO_2$ | $K_2O$ | CaO | | | | |
| 2-1 | Aluminum silicate | 31.4 | 64.0 | 4.2 | 0.4 | | 4.0 | 2.0~6.0 | 1.0 |
| 2-2 | | 32.2 | 63.4 | 3.6 | 0.8 | | 20.0 | 15.0~25.0 | 4.0 |
| | | $Al_2O_3$ | $SiO_2$ | CaO | MgO | | | | |
| 3-1 | Mullite | 70.0 | 25.0 | 4.5 | 0.5 | | 4.0 | 2.0~6.0 | 1.5 |
| 3-2 | | 70.0 | 25.0 | 5.0 | | | 10.0 | 5.0~15.0 | 3.0 |
| 3-3 | | 70.0 | 25.0 | 5.0 | | | 20.0 | 15.0~25.0 | 6.0 |
| | | $Al_2O_3$ | $SiO_2$ | | MgO | | | | |
| 4-1 | Cordierite | 34.9 | 51.4 | | 13.7 | | 4.0 | 2.0~6.0 | 1.5 |
| 4-2 | | 34.0 | 52.0 | | 14.0 | | 10.0 | 5.0~15.0 | 3.0 |
| 4-3 | | 35.3 | 50.2 | | 14.5 | | 20.0 | 15.0~25.0 | 6.0 |
| | | $ZnO_2$ | $Y_2O_3$ | CaO | | | | | |
| 5-1 | Zirconia | 92.0 | | 8.0 | | | 10.0 | 7.0~12.0 | 3.5 |
| 5-2 | | 92.0 | 8.0 | | | | 20.0 | 17.0~23.0 | 5.5 |

| Example | Porosity (%) | Water permeability | Center-line surface roughness (μm) | Occurrence of mold | Clouding of porcelain material | Uniformity of pore distribution |
|---|---|---|---|---|---|---|
| 1-1 | 33.0 | Δ | 1.0 | ○ | ○ | ○ |
| 1-2 | 43.0 | ○ | 1.0 | ○ | ○ | ○ |
| 1-3 | 41.0 | ○ | 1.0 | ○ | ○ | ○ |
| 1-4 | 45.0 | ○ | 1.2 | ○ | ○ | ○ |
| 1-5 | 45.0 | ○ | 1.4 | ○ | ○ | ○ |
| 2-1 | 35.0 | ○ | 1.0 | ○ | ○ | ○ |
| 2-2 | 38.0 | ○ | 1.2 | ○ | ○ | ○ |
| 3-1 | 28.0 | ○ | 1.0 | ○ | ○ | ○ |
| 3-2 | 31.0 | ○ | 1.0 | ○ | ○ | ○ |
| 3-3 | 33.0 | ○ | 1.2 | ○ | ○ | ○ |
| 4-1 | 28.0 | ○ | 1.2 | ○ | ○ | ○ |
| 4-2 | 31.0 | ○ | 1.6 | ○ | ○ | ○ |
| 4-3 | 33.0 | ○ | 1.8 | ○ | ○ | ○ |
| 5-1 | 37.0 | ○ | 1.2 | ○ | ○ | ○ |
| 5-2 | 39.0 | ○ | 1.6 | ○ | ○ | ○ |

TABLE 2

| Example | Composition | Porous ceramics | | | | | | | Antibacterial zeolites | | Grain size distribution (μm) |
|---|---|---|---|---|---|---|---|---|---|---|---|
| | | $Al_2O_3$ | $SiO_2$ | $K_2O$ | CaO | MgO | $ZnO_2$ | $Y_2O_3$ | A type zeolite | X type zeolite | |
| 6 | Alumina | 90 | 10 | | | | | | 0.1 | | 6.0 |
| 7 | Aluminum silicate | 31.4 | 64.0 | 4.2 | 0.4 | | | | 1.0 | | 4.0 |
| 8 | Mullite | 70 | 25 | | 4.5 | 0.5 | | | | 5.0 | 4.0 |
| 9 | Cordierite | 34 | 52 | | | 14.0 | | | | 10.0 | 10.0 |
| 10 | Zirconia | | | | | | 92 | 8.0 | 0.25 | 0.25 | 20.0 |

| Example | Mean grain size (μm) | Mean pore size (μm) | Porosity (%) | Water permeability | Center-line surface roughness (μm) | Occurrence of mold | Clouding of porcelain material | Uniformity of pore distribution |
|---|---|---|---|---|---|---|---|---|
| 6 | 2.0~10.0 | 2.0 | 41.0 | ○ | 1.0 | ⊙ | ○ | ○ |
| 7 | 2.0~6.0 | 1.0 | 35.0 | ○ | 1.0 | ⊙ | ○ | ○ |

TABLE 2-continued

| 8  | 2.0~6.0   | 1.5 | 28.0 | ○ | 1.0 | ◉ | ○ | ○ |
| 9  | 5.0~15.0  | 3.0 | 31.0 | ○ | 1.6 | ◉ | ○ | ○ |
| 10 | 17.0~23.0 | 5.5 | 39.0 | ○ | 1.6 | ◉ | ○ | ○ |

TABLE 3

| Comparative Example | Compositions | Al₂O₃ | SiO₂ | Mean grain size (μm) | Grain size distribution (μm) | Mean pore size (μm) |
|---|---|---|---|---|---|---|
| 1 | Glass | | | | | |
| 2 | Teflon | | | | | |
| 3 | Porcelain material (entire surface glazed) | | | | | |
| 4 | Porcelain material (surface partly glazed) | | | 40.0 | 25.0~55.0 | 20.0 |
| 5 | Alumina | 85.0 | 15.0 | 0.8 | 0.6~0.9 | 0.3 |
| 6 | Porcelain material (partially porous) | | | 40.0 | 25.0~55.0 | 20.0 |
| 7 | Porcelain material (pores) | | | | | |
| 8 | Porcelain material (water absorbed with wick) | | | | | |
| 9 | Alumina | 85.0 | 15.0 | 15.0 | 10.0~20.0 | 5.0 |
| 10 | Alumina | 85.0 | 15.0 | 15.0 | 10.0~20.0 | 5.0 |

| Comparative Example | Porosity (%) | Water permeability | Center line surface roughness | Occurrence of mold | Clouding of porcelain material | Uniformity of Pore distribution |
|---|---|---|---|---|---|---|
| 1 | | X | 0.6 | ○ | ○ | No pore |
| 2 | | X | 0.8 | ○ | ○ | No pore |
| 3 | | X | 1.0 | ○ | ○ | No pore |
| 4 | 40.0 | | 15.0 | X | X | X |
| 5 | 28.0 | | 0.5 | ○ | ○ | ○ |
| 6 | 40.0 | | 15.0 | X | X | X |
| 7 | | | 1.0 | ○ | ○ | No pore |
| 8 | | | 1.0 | ○ | ○ | No pore |
| 9 | 70.0 | ○ | 1.2 | ○ | ○ | ○ |
| 10 | 10.0 | △ | 1.2 | ○ | ○ | ○ |

TABLE 4

| Comparative Example | Composition | Porous ceramics | | | | | | | Antibacterial zeolites | | Grain size distribution (μm) |
|---|---|---|---|---|---|---|---|---|---|---|---|
| | | Al₂O₃ | SiO₂ | K₂O | CaO | MgO | ZnO₂ | Y₂O₃ | A type zeolite | X type zeolite | |
| 11 | Alumina | 90 | 10 | | | | | | 0.005 | | 6.0 |
| 12 | Aluminum silicate | 31.4 | 64.0 | 4.2 | 0.4 | | | | 25 | | 4.0 |
| 13 | Mullite | 70 | 25 | | 4.5 | 0.5 | | | | 0.001 | 4.0 |
| 14 | Cordierite | 34 | 52 | | | 14 | | | | 20 | 10.0 |
| 15 | Zirconia | | | | | | 92 | 8.0 | 8 | 12 | 20.0 |

| Comparative Example | Mean grain size (μm) | Mean pore size (μm) | Porosity (%) | Water permeability | Center-line surface roughness (μm) | Occurrence of mold | Clouding of porcelain material | Uniformity of pore distribution |
|---|---|---|---|---|---|---|---|---|
| 11 | 2.0~10.0 | 2.0 | 41.0 | ○ | 1.0 | X | ○ | ○ |
| 12 | 2.0~6.0 | 0.2 | 35.0 | △ | 8.0 | ◉ | Reddish brown | X |
| 13 | 2.0~6.0 | 1.5 | 28.0 | ○ | 1.0 | X | ○ | ○ |
| 14 | 5.0~15.0 | 0.3 | 31.0 | △ | 13.0 | ◉ | Reddish brown | X |
| 15 | 17.0~23.0 | 0.3 | 39.0 | △ | 6.0 | ◉ | Reddish brown | X |

EFFECT OF THE INVENTION

The dental pallet for handling water-permeable dental porcelain materials according to the present invention provides a solution to various problems of the conventional dental pallets, and is formed of porous ceramics having the properties of having a fine and uniform pore size distribution, as expressed in terms of a mean pore size of 0.5 to 10 μm and a porosity of 15 to 65%. Hence, (1) The present dental pallet of porous ceramics is obtained by carefully regulating a material based on alumina, aluminium silicate, mullite, cordierite, zirconia and vitreous china to the desired grain size distribution, i.e., the grain size ranging from 1.0 μm to 30.0 μm and the mean grain size ranging from 1.5 μm to 25.0 μm, thereby providing a uniform dispersion of fine and uniform pores through porous ceramics, as expressed in terms of a mean pore size of 0.5 to 10 μm and a porosity of 15 to 65%. The surface roughness of the pallet is so reduced that a dental porcelain slurry can be smoothly dished out with a brush and the brush can be substantially protected from abrasion even when it is rubbed against the surface of the pallet.

(2) The kneading plane of the dental pallet of the present invention has a centerline surface roughness as fine as 2.0 μm. Thus, it is unlikely that a metallic spatula used to knead distilled water or the kneading liquid with dental porcelain powders may be worn out by contacting the surface of the pallet. It is consequently unlikely that the prepared porcelain crowns may become cloudy, since the dental porcelain slurry is not contaminated with powders which are otherwise produced by the abrasion of the metallic brush or pallet.

(3) Since the dental pallet is formed of ceramics in which fine and uniform pores are uniformly dispersed, distilled water or the kneading liquid can be stably picked up on the kneading plane from the bottom of the pallet, so that the kneaded dental porcelain slurry can have a constant consistency, thus making dental handling easy.

(4) Since the dental pallet is formed of ceramics in which fine and even pores are uniformly dispersed, the penetration of distilled water or the kneading liquid takes place stably even at both ends of the kneading plane, thus keeping the consistency of a dental porcelain slurry constant. This eliminates the need of frequently kneading the dental porcelain slurry, and so makes it possible for a dental technician to devotedly carry out dental porcelain material-casting work needing attention.

(5) Because of the pores being of fine size, it is unlikely that the kneading plane, etc. may get moldy, even when the dental pallet is immersed in distilled water or the kneading liquid, thus keeping the pallet hygienic. In order to obtain a antimycotic effect over extended periods of time, antibacterial zeolites may be used.

(6) The rate of permeation of distilled water or the kneading liquid through the pallet of the above materials is higher than that through conventional vitreous china ones. Since the pores are uniformly dispersed throughout the pallet, sponge needed for conventional dental porcelain pallets can be dispensed with, so that the pallet can be kept stable, thus making dental handling easy.

Thus, the dental pallet for handling water-permeable dental porcelain materials according to the present invention provides a solution to various problems of the conventional dental porcelain pallets, and makes it possible to carry out dental handling for preparing porcelain crowns in a speedy and successful manner. The present invention thus makes a great contribution to the dental field.

What is claimed is:

1. A pallet for handling water-permeable dental porcelain materials, comprising a porous ceramic material formed of one or two or more selected from the group consisting of materials based on alumina, aluminium silicate, mullite, cordierite, zirconia and vitreous china and having a grain size of 1.0 to 30.0 μm and a mean grain size of 1.5 to 25.0 μm, said porous ceramic material having fine and even pores uniformly dispersed therethrough, as expressed in terms of a porosity of 15 to 65% and a mean pore size of 0.5 to 10 μm.

2. The pallet as claimed in claim 1, wherein the kneading plane of said pallet has a centerline surface roughness of 2.0 μm or below.

3. The pallet as claimed in claim 1, wherein said porous ceramic material contains an antibacterial zeolite.

4. The pallet as claimed in claim 3, wherein said antibacterial zeolite has the formula:

$$XM_{2/n}O \cdot Al_2O_3 \cdot YSiO_2 \cdot ZH_2O$$

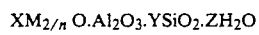

wherein:
M is an ion-exchangeable ion selected from the group consisting of monovalent metal ions, divalent metal ions or ammonium ion,
n is the valence of the metal ion,
X and Y are the index of a metal oxide and silica, respectively, and
Z is the number of water of crystallization.

5. The pallet as claimed in claim 4, wherein said antibacterial zeolite is selected from the group consisting of A type zeolite, X type zeolite, Y type zeolite, T type zeolite, high-silica zeolite, sordalite, mordenite, analcime, cryptolite, chabasite and erionite.

6. The pallet as claimed in claim 4, wherein said ion-exchangeable ion is selected from the group consisting of ammonium ions, silver ions, copper ions, zinc ions, bismuth ions and thallium ions.

7. The pallet as claimed in claim 1, wherein the amount of said antibacterial zeolite added to said porous ceramic is 0.005 to 15 parts by weight per 100 parts by weight of the latter.

* * * * *